United States Patent [19]

Sekiguchi et al.

[11] Patent Number: 4,545,939

[45] Date of Patent: Oct. 8, 1985

[54] PROCESS FOR PRODUCING SULFONATE OF UNSATURATED FATTY ACID ESTER

[75] Inventors: Shizuo Sekiguchi, Funabashi; Kyozo Kitano, Narashino; Katsumasa Nagano, Ichikawa, all of Japan

[73] Assignee: Lion Corporation, Tokyo, Japan

[21] Appl. No.: 626,081

[22] Filed: Jun. 29, 1984

[30] Foreign Application Priority Data

Jul. 1, 1983 [JP] Japan ............................ 58-119776
Dec. 27, 1983 [JP] Japan ............................ 58-249689

[51] Int. Cl.$^4$ ............................................. C07C 143/90
[52] U.S. Cl. ................................................... 260/400
[58] Field of Search ........................................ 260/400

[56] References Cited

U.S. PATENT DOCUMENTS

| | | | |
|---|---|---|---|
| 1,185,213 | 5/1916 | Levinstein | 260/400 |
| 1,822,979 | 9/1931 | Munz | 260/400 |
| 1,823,815 | 9/1931 | Bertsch | 260/400 |
| 2,032,313 | 2/1936 | Bertsch | 260/400 |
| 2,195,187 | 3/1940 | Moyer | 260/400 |
| 2,352,698 | 7/1944 | Eaton et al. | 260/400 |
| 2,367,050 | 1/1945 | Price et al. | 260/400 |

FOREIGN PATENT DOCUMENTS 387398 2/1933 United Kingdom ............... 260/400

*Primary Examiner*—J. E. Evans
*Attorney, Agent, or Firm*—Armstrong, Nikaido, Marmelstein & Kubovcik

[57] ABSTRACT

A process for producing a sulfonate of an unsaturated fatty acid lower alkyl ester comprising the steps of:

(i) sulfonating a mixture of (A) a lower alkyl ester of an unsaturated $C_8$ to $C_{22}$ fatty acid and (B) a lower alkyl ester of a saturated $C_8$ to $C_{22}$ fatty acid in a weight ratio of (A)/(B)=90/10 to 5/95 with a sulfonating agent in such a manner that the amount of the unreacted component (A) in the total unreacted components in the mixture is at least 0.3% by weight; and (ii) neutralizing and hydrolyzing the sulfonated product.

This process provides the desired sulfonate of unsaturated fatty acid ester having a pale tone color at a high conversion. When the sulfonated product is separated by using (a) a polyol (or polyhydric alcohol) having 2 to 8 carbon atoms, (b) an alkylene glycol in a liquid state at an ambient temperature, or (c) an olefin having 6 to 30 carbon atoms, the desired sulfonate can be separated at a high recovery efficiency and with good workability.

7 Claims, No Drawings

PROCESS FOR PRODUCING SULFONATE OF UNSATURATED FATTY ACID ESTER

BACKGROUND OF THE INVENTION

1. Field of the Invention

The present invention is a process for producing a sulfonate of an unsaturated fatty acid ester. More specifically, it relates to a process for producing a sulfonate of an unsaturated fatty acid ester at a high conversion without causing discoloration by using, as a reacting solvent, a saturated fatty acid ester. Futhermore, it relates to a process for producing a sulfonate of an unsaturated fatty acid ester at a high recovery efficiency and with good workability.

2. Description of the Prior Art

Sulfonation of saturated fatty acid esters can be effected by known methods, as disclosed in, for example, Japanese Examined Patent Publication (Kokoku) Nos. 39-20842, 39-28635, and 41-965. The sulfonates can be neutralized and hydrolyzed to obtain the desired sulfonates having a pale tone color at a high conversion. However, when the above-mentioned sulfonation methods are applied to sulfonation of an unsaturated fatty acid ester, the desired sulfonated products cannot be obtained at a high conversion. If a mole ratio of a sulfonating agent such as $SO_3$ to an unsaturated fatty acid ester is increased, not only is the desired high conversion not necessarily obtained, but also the color of the resultant sulfonated product is remarkably decreased due to the formation of polysulfonates having 2 or more sulfonic acid groups therein.

Sulfonates of unsaturated fatty acid esters, advantageously provide detergent compositions having an excellent foaming power, detergent power, and penetrating power as well as a good rinsing property by formulating the sulfonates of unsaturated fatty acid esters with sulfonates of saturated fatty acid esters into the detergent compositions. Recently, sulfonates of unsaturated fatty acid esters have been especially noted as a surfactant. Consequently, there is a demand that sulfonates of unsaturated fatty acid esters having a pale tone color suitable for use in a detergent composition be produced at a high conversion.

SUMMARY OF THE INVENTION

Accordingly, the objects of the present invention are to eliminate the above-mentioned problems in the prior art and to provide a process for producing a sulfonate of an unsaturated fatty acid ester having a pale tone color at a high conversion.

Another object of the present invention is to provide a process for producing a sulfonate of an unsaturated fatty acid ester at a high recovery efficiency and with good workability.

Other objects and advantages of the present invention will be apparent from the description set forth hereinbelow.

In accordance with the present invention, there is provided a process for producing a sulfonate of an unsaturated fatty acid lower alkyl ester comprising the steps of:

(i) sulfonating a mixture of (A) a lower alkyl ester of an unsaturated $C_8$ to $C_{22}$ fatty acid and (B) a lower alkyl ester of a saturated $C_8$ to $C_{22}$ fatty acid in a weight ratio of $(A)/(B) = 90/10$ to $5/95$ with a sulfonating agent in such a manner that the amount of the unreacted component (A) in the total unreacted components in the mixture is at least 0.3% by weight; and (ii) neutralizing and hydrolyzing the sulfonated product.

DESCRIPTION OF THE PREFERRED EMBODIMENTS

According to the present invention, the unsaturated fatty acid esters (A) are sulfonated together with the saturated fatty acid esters (B). The sulfonation reactivity of the unsaturated fatty acid esters (A) is far higher than that of the saturated fatty acid esters (B) (i.e., $(A) >> (B)$). The present inventors have found that, when a mixture of the components (A) and (B) is sulfonated, the component (A) is preferentially sulfonated to form an addition product thereof with 1 mol of $SO_3$ and, therefore, the desired sulfonate of the unsaturated fatty acid ester is obtained at an high conversion, when compared with the sulfonation of the component (A) alone, due to the presence of the component (B), wherein the component (B) appears to act as a good reaction solvent. Futhermore, when the sulfonation reaction proceeds further, the polysulfonated products of the component (A) and the sulfonated product of the component (B) are concurrently produced and, as a result, the remarkable and non-preferable discoloration of the sulfonated product occurs. It has also been found that the formation rate of the polysulfonated product of the component (A) is faster than that of the sulfonated product of the component (B).

According to the present invention, the sulfonation of the component (A) must be carried out in a mixture of the components (A) and (B) at a weight ratio of $(A)/(B) = 90/10$ to $5/95$, preferably 80/20 to 10/90. When the above-mentioned ratio $(A)/(B)$ is larger than 90/10, the desired conversion is decreased due to the fact that the solvent effect of the saturated fatty acid ester cannot be sufficiently effected. Contrary to this, when the above-mentioned ratio $(A)/(B)$ is smaller than 5/95, the yield (or the produced amount) of the desired sulfonate of the unsaturated fatty acid ester is decreased, which is not preferable from a practical viewpoint.

The unsaturated fatty acid esters usable as the component (A) in the present invention are the lower alkyl esters of unsaturated fatty acids having fatty acid residues with 8 to 22 carbon atoms. The suitable lower alkyl groups are those having 1 to 6 carbon atoms. Of these unsaturated fatty acid esters, the use of the lower alkyl esters of unsaturated fatty acids having the lower alkyl groups with 1 to 3 carbon atoms and the fatty acid residues with 12 to 18 carbon atoms is preferable. These unsaturated fatty acid esters may be used alone or in any mixture therof.

The saturated fatty acid esters usable as the component (B) in the present invention are the lower alkyl esters of saturated fatty acids having fatty acid residues with 8 to 22 carbon atoms. The suitable lower alkyl groups are those having 1 to 6 carbon atoms. Of these saturated fatty acid esters, the use of the lower alkyl esters of saturated fatty acids having the lower alkyl group with 1 to 3 carbon atoms and the fatty acid residues with 12 to 18 carbon atoms is preferable. These saturated fatty acid esters may be used alone or in any mixture thereof.

The sulfonation can be carried out in any conventional manner. For example, the mixture of the components (A) and (B) is sulfonated by using a thin-film type sulfonation method or vessel type sulfonation method, preferably at a temperature of 30° C. to 120° C., more preferably 40° C. to 90° C. As a sulfonating agent, liquid $SO_3$, gaseous $SO_3$ (e.g., diluted with an inert gas such as nitrogen or air), oleum, chlorosulfonic acid, or any other conventional sulfonating agent can be used in the practice of the present invention. The preferable mol ratio of the sulfonating agent, in terms of $SO_3$, to the mixture of the components (A) and (B) is 0.5 to 2.0, more preferably 1.0 to 1.5.

According to the present invention, the sulfonation must be carried out in such a manner that the component (A) is preferentially sulfonated and that the sulfonation reaction is terminated when the content of the unreacted component (A) in the total unreacted oil is 0.3% by weight or more, preferably 0.3% to 5% by weight, so that the polysulfonated product of the component (A) and the sulfonated product of the component (B) are not substantially formed. When the sulfonation is continued until the content of the unreacted component (A) in the total amount of the unreacted components (A) and (B) is less than 0.3% by weight, the sulfonated product is discolored due to the fact that the polysulfonation and the other reactions proceed. There is no upper limit of the content of the unreacted component (A) in the total amount of the unreacted components (A) and (B) at which the sulfonation must be terminated. However, the preferable upper limit of the content of the unreacted component (A) is 5% of weight taking into consideration the conversion of the desired sulfonation reaction.

The unreacted component (B) containing 0.3% by weight, preferably 0.3% to 5% by weight, of the component (A) is recovered from the sulfonated product as mentioned hereinbelow and the unreacted component (B) thus recovered can be separately sulfonated together with a small amount of the unreacted component (A). Thus, the sulfonated product containing, as a main constituent, the sulfonate of the saturated fatty acid ester and having a good color can be obtained. For this reason, when the sulfonates of the unsaturated fatty acid esters are first produced, and subsequently the sulfonates of the saturated fatty acid esters are produced from the saturated-unsaturated mixed fatty acid esters, the content of the unreacted component (A) in the unreacted oil (i.e., the total amount of the components (A) and (B)) is preferably 0.3% to 5% by weight, more preferably 0.5% to 2% by weight.

The sulfonated products are neutralized and hydrolyzed in a conventional manner and the sulfonate of the unsaturated fatty acid esters are separated. In the practice of the sulfonation according to the present invention, hydroxysulfonates having no double bond obtained from the addition of a hydroxy group to a double bond during the sulfonation or formed by hydrolizing sultones are contained in the sulfonated products of the unsaturated fatty acid esters. According to the present invention, the sulfonated products are neutralized and hydrolyzed in any conventional manner. For example, the neutralization can be carried out, at a temperature of 40° C. to 80° C., by using an oxide or hydroxide of an alkali metal, such as sodium, potassium, or lithium, or an alkaline earth metal, such as magnesium or calcium, or an organic base such as ammonia, ethanolamine, diethanolamine, or triethanolamine. Generally, the hydrolyzation can be carried out at a temperature of 60° C. to 200° C. for 1 to 180 minutes.

The neutralized and hydrolyzed products are then generally subjected to any conventional separation method, such as a hexane extraction, a stationary phase separation after an alcohol addition, or a centrifugal separation, whereby an unreacted oil is recovered. Thus, the sulfonates of the unsaturated fatty acid esters can be obtained.

According to the preferred embodiment of the present invention, the resultant sulfonates of the unsaturated fatty acid esters can be obtained by efficiently and simply separating the unreacted oil from the sulfonated, neutralized, and hydrolyzed products by adding thereto at least one separating auxiliary selected from the group consisting of (a) polyols (or polyhydric alcohols) having 2 to 8 carbon atoms, (b) alkylene glycols which are liquid at an ambient temperature, and (c) olefins having 6 to 30 carbon atoms, followed by stationary phase separation.

Examples of the polyols preferably usable as a separating auxiliary in the present invention are glycerine and polyglycerine.

Examples of the alkylene glycols preferably usable as a separating auxiliary in the present invention are ethylene glycol, propylene glycol, diethylene glycol, triethylene glycol, dipropylene glycol, glycerine, polyethylene glycol #400, polyethylene glycol #600, and polypropylene glycol.

Examples of the olefins preferably usable as a separating auxiliary in the present invention are internal olefins having 8 to 20 carbon atoms.

The preferable separating auxiliaries are ethylene glycol, propylene glycol, diethylene glycol, glycerine, $C_{10}$ internal olefin, $C_{12}$ internal olefin, and $C_{14}$ internal olefins.

The separating auxiliary is preferably added to the sulfonated products in an amount of 30% to 500% by weight, more preferably 50% to 200% by weight, based on the amount of the sulfonate of the unsaturated fatty acid ester. The sulfonated products are then allowed to stand at a temperature of 80° C. to 200° C., preferable 100° C. to 150° C. for 1 to 120 minutes. Thus, when the separating auxiliary is water-soluble, an aqueous phase containing the desired sulfonate of the unsaturated fatty acid ester and the separating auxiliary and an oil phase mainly containing the saturated fatty acid ester are separated. When the separating auxiliary is slight soluble or insoluble in water, an aqueous phase containing the sulfonate and the unsaturated fatty acid ester and an oil phase containing the saturated fatty acid ester and the separating auxiliary are separated. In the former case, the aqueous phase can be directly used, but the separating auxiliary can be optionally separated from the aqueous phase by means of a thin-film evaporation. In the latter case, an aqueous phase can be recovered by any optional means such as decantation or by using a separating funnel, whereby the desired sulfonate of the unsaturated fatty acid ester can be readily obtained.

The unreacted oil thus recovered and mainly containing the saturated fatty acid ester can be recycled to the sulfonation step to be mixed with the component (A) or can be separately sulfonated in a separate step to produce the sulfonates of the saturated fatty acid ester.

As mentioned above, according to the present invention, the desired sulfonates of unsaturated fatty acid esters having a pale tone color can be prepared at a high conversion by sulfonating unsaturated fatty acid esters in the presence of the specified amount of the saturated fatty acid esters.

Furthermore, according to the present invention, the desired sulfonate of the unsaturated fatty acid esters containing no substantial amounts of the saturated fatty acid esters and separating auxiliary can be readily obtained by an extremely simple method, that is, by adding the separating auxiliary, followed by the stationary separation.

EXAMPLES

The present invention will now be further illustrated by, but is by no means limited to, the following Examples.

EXAMPLE 1

In Run No. A, non-hydrogenated palm oil fatty acid methyl ester having an unsaturated ester content of 42% by weight and an average molecular weight of 281 was sulfonated in a laboratory type glass thin-film type reactor under the conditions of an $SO_3$ mole ratio of 1.2 and a reaction temperature of 80° C. The sulfonated product was neutralized by using a 5% aqueous sodium hydroxide solution.

A portion of the neutralized product thus obtained was sampled and the unreacted oil was extracted by petroleum ether. The content of the unreacted unsaturated fatty acid ester contained in the unreacted oil determined by the measurement of the iodine value was 0.7% by weight.

Furthermore, the sulfonation conversion of the unsaturated fatty acid esters was calculated from the content of the unsaturated fatty acid ester in the starting material before the sulfonation and the content of the unsaturated fatty acid ester in the unreacted oil. The conversion was 98.2%.

The sulfonate of the unsaturated fatty acid ester was obtained by removing the unreacted oil from the neutralized product. The sulfonate of the unsaturated fatty acid ester thus obtained was dissolved in water and the color tone of 5% aqueous solution of the sulfonate was determined by using a 40×10 mm quartz cell in a KLETT-Summerson photoelectric colorimeter. The result was 3700 (the smaller the value, the better the color tone).

Run Nos. B to I were carried out in the same manner as mentioned above, except that the starting materials and the sulfonation conditinos listed in Table 1 were used.

The results of Run Nos. A to I are summarized in Table 1.

TABLE 1

| Run No. | A | B | C | D | E | F | G | H | I |
|---|---|---|---|---|---|---|---|---|---|
| Starting material | Palm oil fatty acid methyl ester | | | | 1:1 mixture of palm oil fatty acid methyl ester and methyl oleate | | Tallow fatty acid methyl ester | Methyl oleate | |
| Unsaturated ester content in the starting material (wt %) | 42 | | | | 68 | | 45 | 95 | |
| Sulfonation conditions $SO_3$ mole ratio | 1.2 | 0.9 | 2.5 | 0.6 | 1.1 | 3.6 | 1.2 | 4.5 | 3.0 |
| Temperature (°C.) | 80 | 80 | 80 | 80 | 80 | 80 | 80 | 80 | 80 |
| Unsaturated ester content in unreacted oil (wt %) | 0.7 | 3.0 | 0.1 | 6.0 | 0.8 | 0.1 | 0.7 | 0.2 | 0.7 |
| Conversion (%) | 98.2 | 94.6 | 99.3 | 89.6 | 98.1 | 99.5 | 98.3 | 99.1 | 98.3 |
| Color tone | 3700 | 2500 | 45000 | 2000 | 4200 | 52000 | 3500 | 60000 | 35000 |

A 1 kg amount of the neutralized product obtained in each run mentioned above was thoroughly mixed with 1 kg of ethanol, while agitating. The mixture was extracted three times with 500 ml each of petroleum ether. The petroleum ether layer was topped in vacuo in a rotary evaporator to recover the unreacted oil.

The unreacted oil thus recovered was sulfonated in a glass thin-film type reactor under the conditions of a $SO_3$ mol ratio of 1.5 and a reaction temperature of 80° C. in the same manner as mentioned above. The sulfonated product was neutralized with a 5% aqueous NaOH solution. The conversion and the color were determined in the same manner as mentioned above. The results are shown in Table 2.

The sulfonated product of the saturated fatty acid ester obtained above was mixed with the aqueous ethanol layer (containing the sulfonated product of the unsaturated fatty acid ester) obtained by removing the unreacted oil by the petroleum ether extraction in such a manner that a equi-amount mixture of the sulfonates of the saturated and unsaturated fatty acid esters in terms of the solid content was formed.

The conversion and the color of the mixture were determined in the same manner as mentioned above. The results are shown in Table 2.

TABLE 2

| Run No. | | A' | B' | C' | D' | E' | F' | G' | H' | I' |
|---|---|---|---|---|---|---|---|---|---|---|
| Sulfonation starting Unreacted material | | Unreacted oil in Run No. A | Unreacted oil in Run No. B | Unreacted oil in Run No. C | Unreacted oil in Run No. D | Unreacted oil in Run No. E | Unreacted oil in Run No. F | Unreacted oil in Run No. G | oil in Run No. H | oil in Run No. I |
| Unsaturated ester content in starting material (%) | | 0.7 | 3.0 | 0.1 | 6.0 | 0.8 | 0.1 | 0.7 | 0.2 | 0.7 |
| Conversion (%) | | 93 | 78 | 98 | 72 | 93 | 98 | 93 | 98 | 93 |
| Color tone | | 6500 | 37000 | 4700 | 48000 | 5700 | 4200 | 6700 | 4300 | 6900 |
| Mixture properties | Mixture (saturated/unsaturated) | A'/A | B'/B | C'/C | D'/D | E'/E | F'/F | G'/G | H'/H | I'/I |
| | Mixing ratio (saturated/ | 1/1 | 1/1 | 1/1 | 1/1 | 32/68 | 32/68 | 55/45 | 5/95 | 5/95 |

TABLE 2-continued

| Run No. | A' | B' | C' | D' | E' | F' | G' | H' | I' |
| --- | --- | --- | --- | --- | --- | --- | --- | --- | --- |
| unsaturated) | | | | | | | | | |
| Conversion (%) | 96 | 89 | 98 | 85 | 98 | 99 | 96 | 99 | 99 |
| Color tone | 4600 | 19000 | 25000 | 25000 | 4600 | 38000 | 5100 | 57000 | 34000 |

EXAMPLE 2

A 40/60 mixture (by weight) of methyl oleate and extremely hardened palm oil fatty acid methyl ester was sulfonated in a glass thin-film type reactor under the conditions of $SO_3$ mole ratio of 1.2 and a reaction temperature of 70° C. to 80° C., followed by neutralization and hydrolysis.

A separating auxiliary listed in Table 3 was then added to the product obtained above while mixing and the mixture was allowed to stand at a temperature listed in Table 3 for 30 minutes. Thus, the unreacted oil was recovered.

The contents of the unreacted oil in the mixture, based on the sulfonate of the unsaturated fatty acid ester, before and after the separation were determined. The results are shown in Table 3. In Run No. Q, palm kernel methyl ester was used in lieu of the extremely hardened palm oil fatty acid methyl ester.

TABLE 3

| Run No. | | J | K | L** | M** | N** | O** | P | Q** |
| --- | --- | --- | --- | --- | --- | --- | --- | --- | --- |
| Separating auxiliary | | None | n-hexane | Ethylene glycol (EG) | Propylene glycol | Internal olefin (IO) | EG/IO = 5/5 | Ethanol | Ethylene glycol |
| Amount of separating auxiliary* | | — | 200 | 100 | 200 | 200 | 150 | 200 | 100 |
| Separation temperature (°C.) | | 150 | 25 | 150 | 150 | 150 | 150 | 70 | 150 |
| Unreacted oil content* | Before separation | 150 | 150 | 150 | 150 | 150 | 150 | 150 | 150 |
| | After separation | 100 | 120 | 7.0 | 6.6 | 6.5 | 3.9 | 72 | 6.8 |

*% by weight, based on the sulfonate of the unsaturated fatty acid ester
**Preferable embodiment

We claim:

1. A process for producing a sulfonate of an unsaturated fatty acid lower alkyl ester comprising the steps of:
   (i) sulfonating a mixture of (A) a lower alkyl ester of an unsaturated $C_8$ to $C_{22}$ fatty acid and (B) a lower alkyl ester of a saturated $C_8$ to $C_{22}$ fatty acid in a weight ratio of (A)/(B)=90/10 to 5/95 with a sulfonating agent in such a manner that the amount of the unreacted component (A) in the total unreacted components in the mixture is at least 0.3% by weight; and
   (ii) neutralizing and hydrolyzing the sulfonated product.

2. A process as claimed in claim 1, which further comprises separating the sulfonate of the unsaturated fatty acid lower alkyl ester from other constituents of the neutralized and hydrolyzed product by adding at least one polyol having 2 to 8 carbon atoms, as a separating auxiliary, to the neutralized and hydrolyzed product, followed by removing the unsaturated fatty acid lower alkyl ester from the neutralized and hydrolyzed product by phase separation.

3. A process as claimed in claim 2, wherein the separation is carried out by adding 30% to 500% by weight, based on the sulfonate of the unsaturated fatty acid lower alkyl ester sulfonate, of the separating auxiliary to the neutralized and hydrolized product and by allowing the mixture to stand at a temperature of 80° C. to 120° C. for 1 to 120 minutes.

4. A process as claimed in claim 1, which further comprises separating the sulfonate of the unsaturated fatty acid lower alkyl ester from other constituents of the neutralized and hydrolyzed product by adding, as a separating auxiliary, at least one alkylene glycol in a liquid state at an ambient temperature to the neutralized and hydrolyzed product, followed by removing the unsaturated fatty acid lower alkyl ester from the neutralized and hydrolyzed product by phase separation.

5. A process as claimed in claim 4, wherein the separation is carried out by adding 30% to 500% by weight, based on the sulfonate of the unsaturated fatty acid lower alkyl ester sulfonate, of the separating auxiliary to the neutralized and hydrolyzed product and by allowing the mixture to stand at a temperature of 80° C. to 120° C. for 1 to 120 minutes.

6. A process as claimed in claim 1, which further comprises separating the sulfonate of the unsaturated fatty acid lower alkyl ester from other constituents of the neutralized and hydrolyzed product by adding, as a separating auxiliary, at least one olefin having 6 to 30 carbon atoms to the neutralized and hydrolyzed product, followed by removing the unsaturated fatty acid lower alkyl ester from the neutralized and hydrolyzed product by phase separation.

7. A process as claimed in claim 6, wherein the separation is carried out by adding 30% to 500% by weight, based on the sulfonate of the unsaturated fatty acid lower alkyl ester sulfonate, of the separating auxiliary to the neutralized and hydrolyzed product and by allowing the mixture to stand at a temperature of 80° C. to 120° C. for 1 to 120 minutes.

* * * * *